(12) United States Patent
Berentsveig et al.

(10) Patent No.: US 8,591,807 B2
(45) Date of Patent: Nov. 26, 2013

(54) MEMBRANE STERILIZATION

(75) Inventors: Vladimir Berentsveig, Alexandria (AU);
Ron Weinberger, Alexandria (AU)

(73) Assignee: Saban Ventures Pty Limited,
Alexandria (AU)

(*) Notice: Subject to any disclaimer, the term of this patent is extended or adjusted under 35 U.S.C. 154(b) by 534 days.

(21) Appl. No.: 11/997,850

(22) PCT Filed: Aug. 4, 2006

(86) PCT No.: PCT/AU2006/001114
§ 371 (c)(1),
(2), (4) Date: Feb. 4, 2008

(87) PCT Pub. No.: WO2007/014436
PCT Pub. Date: Feb. 8, 2007

(65) Prior Publication Data
US 2008/0240981 A1    Oct. 2, 2008

(30) Foreign Application Priority Data

| Aug. 4, 2005 | (AU) | ................................ | 2005904181 |
| Aug. 4, 2005 | (AU) | ................................ | 2005904196 |
| Aug. 4, 2005 | (AU) | ................................ | 2005904198 |
| Feb. 15, 2006 | (AU) | ................................ | 2006900748 |

(51) Int. Cl.
*A61L 2/00*    (2006.01)
*A61L 2/18*    (2006.01)
*A61L 9/00*    (2006.01)

(52) U.S. Cl.
USPC .......................................................... 422/28

(58) Field of Classification Search
USPC .......................................................... 422/28
See application file for complete search history.

(56) References Cited

U.S. PATENT DOCUMENTS 3,481,689 A    12/1969    Rosdahl et al.
3,950,247 A    4/1976    Chiang et al.
(Continued)

FOREIGN PATENT DOCUMENTS

EP    679407    11/1995
GB    663720    12/1951
(Continued)

OTHER PUBLICATIONS

Ex parte Lin BPAI Decision, sent by applicant's attorney on Nov. 7, 2012.*

(Continued)

*Primary Examiner* — Walter D Griffin
*Assistant Examiner* — Christopher Vandeusen
(74) *Attorney, Agent, or Firm* — Senniger Powers LLP

(57) ABSTRACT

A method for disinfecting or sterilizing an article comprising enclosing the article or article part inside a container having a wall of which at least a part is a semipermeable fabric or membrane and introducing an amount of vaporizable biocide, preferably hydrogen peroxide in water, to the interior of said container in solution, vapor, liquid or preferably nebulant form. The semipermeable fabric or membrane is selected to allow the biocide to pass from inside to outside of the container as a vapor at atmospheric pressure and to provide a barrier against entry of micro-organisms. The biocide is allowed to exit the container through said membrane while at or above atmospheric pressure, a fluid eg air is directed to flow adjacent the outside of the membrane to expedite vapor removal from the interior side. The article is exposed to the biocide for a time sufficient to disinfect or sterilize the article.

28 Claims, 13 Drawing Sheets

(56) References Cited

U.S. PATENT DOCUMENTS

Figure 1:
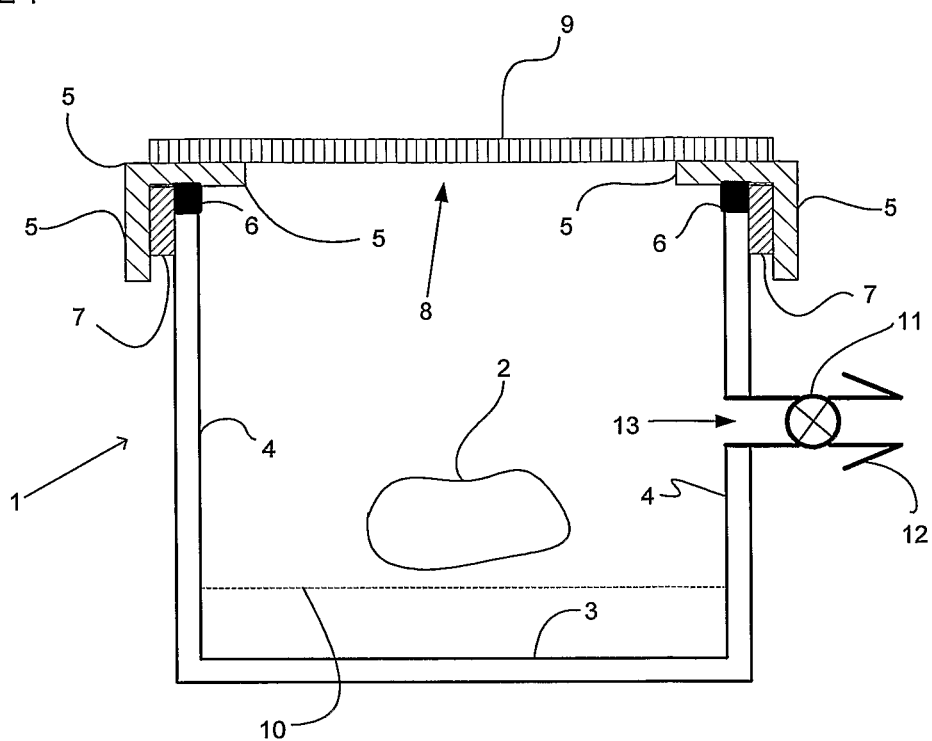

| | | | |
|---|---|---|---|
| 4,022,324 A | | 5/1977 | Schuster |
| 4,191,543 A | * | 3/1980 | Peters .............................. 96/223 |
| 4,296,068 A | | 10/1981 | Hoshino |
| 4,366,125 A | | 12/1982 | Kodera et al. |
| 4,680,163 A | | 7/1987 | Blidschun et al. |
| 4,718,985 A | | 1/1988 | Kjellander |
| 4,744,951 A | | 5/1988 | Cummings et al. |
| 4,958,529 A | * | 9/1990 | Vestal ......................... 73/864.81 |
| 4,978,430 A | | 12/1990 | Nakagawa et al. |
| 5,454,274 A | | 10/1995 | Zhu |
| 5,611,842 A | | 3/1997 | Friesen et al. |
| 5,843,209 A | | 12/1998 | Ray et al. |
| 5,851,485 A | | 12/1998 | Lin et al. |
| 6,066,294 A | * | 5/2000 | Lin et al. ......................... 422/28 |
| 6,325,972 B1 | | 12/2001 | Jacobs et al. |
| 6,379,616 B1 | | 4/2002 | Sheiman |
| 6,500,465 B1 | | 12/2002 | Ronlay |
| 6,656,426 B1 | | 12/2003 | Wang et al. |
| 6,977,061 B2 | | 12/2005 | Lin et al. |
| 7,014,813 B1 | | 3/2006 | Watling et al. |
| 7,122,166 B2 | | 10/2006 | Parrish |
| 7,326,382 B2 | | 2/2008 | Adiga et al. |
| 2002/0119075 A1 | | 8/2002 | Jacobs et al. |
| 2003/0143110 A1 | * | 7/2003 | Kritzler et al. .................. 422/29 |
| 2003/0183576 A1 | * | 10/2003 | Ohara et al. .................. 210/650 |
| 2003/0192799 A1 | * | 10/2003 | Addy et al. .................... 206/364 |
| 2004/0022673 A1 | * | 2/2004 | Protic ............................. 422/28 |
| 2004/0062692 A1 | | 4/2004 | Lin et al. |
| 2005/0252856 A1 | | 11/2005 | Parrish |

FOREIGN PATENT DOCUMENTS

| | | | |
|---|---|---|---|
| GB | 1138512 | | 1/1969 |
| GB | 2346095 A | | 8/2000 |
| JP | 55-137007 | | 10/1980 |
| JP | 60-206408 | | 10/1985 |
| JP | S60220067 | | 11/1985 |
| JP | 63-175602 | | 7/1988 |
| JP | 02-273518 | | 11/1990 |
| JP | 10-284458 | | 10/1998 |
| JP | 2003-095617 | | 4/2003 |
| JP | 2003-180802 | | 7/2003 |
| JP | 2004-267755 | | 9/2004 |
| WO | 9111374 | | 8/1991 |
| WO | 9966961 A1 | | 12/1999 |
| WO | WO 01/21223 | * | 3/2001 |
| WO | 02/056988 A2 | | 7/2002 |
| WO | 2004073827 | | 9/2004 |

OTHER PUBLICATIONS

International Search Report, PCT/AU2006/001114, dated Sep. 1, 2006, 2 pages.
International Preliminary Report on Patentability, PCT/AU2006/001114, dated Jul. 30, 2007, 3 pages.
McDonnell, G., et al., "Antiseptics and Disinfectants: Activity, Action, and Resistance," 1999, Clin Microbiol Rev, 12/1:147-179.
"Content and Format of Premarket Notification [510(k)] Submissions for Liquid Chemical Sterilants/High Level Disinfectants," Jan. 3, 2000, Guidance for Industry and FDA Reviewers, CDRH, 59 pages.
"Explanation of HMIS Ratings," obtained from http://www.paint.org/componentfdocman/cat_view/49-hmis.html on Feb. 10, 2012, 2 pages.
English translation of Office Action issued in Japanese Patent Application No. 2008-524316, mailed Nov. 29, 2011, provides brief description of JP S60220067 for which no English translation is available. 5 pages.
Material Safety Data Sheet, Ethanol Solution, Sigma-Aldrich Corporation, Version 3.1, Revised Jul. 12, 2011, Printed Feb. 10, 2012, 7 pages.
Material Safety Data Sheet, Hydrogen Peroxide Solutions Greater Than 60%, FMC MSDS Ref. No. 7722-84-1-5, Date Approved May 21, 2011, Revision No. 12, 11 pages.
Material Safety Data Sheet, Peracetic Acid, 35% MSDS, Sciencelab.com, created Oct. 10, 2005, Updated Nov. 1, 2010, 7 pages.

* cited by examiner

Insert probe into bag
gather opening of bag
around cable gland

A

Wrap sealing tape around
cable gland to cover
bag opening

B

MEMBRANE STERILIZATION

FIELD OF THE INVENTION

This invention relates to a method for disinfecting or sterilizing a surface and is a modification or improvement of the invention described in our co-pending application entitled "Improved Aerosol" the content of which is incorporated herein by reference. The method has particular application for disinfecting or sterilizing medical instruments but is not limited to that use.

While the invention is capable of sterilization, it will be understood that the invention may also advantageously be used for disinfection, and high level disinfection. References herein to sterilization include disinfection where the context so admits.

BACKGROUND OF THE INVENTION

In our co-pending application there is described a method for disinfecting or sterilizing a surface comprising the steps of:

(1) nebulising a solution comprising a sterilizing agent in a solvent to form a nebulant of finely divided particles of the solution in a gas stream, said solution including a solvent having a lower boiling point than the sterilizing agent;

(2) subjecting the nebulant to energy of a kind and for a duration sufficient to vaporize solvent in preference to sterilizing agent, whereby to increase the concentration of the agent in the nebulant particles;

(3) removing solvent vaporized in step 2 from the gas stream at or above atmospheric pressure and, if necessary, cooling the nebulant to below 70° C.; and (4) exposing said surface to nebulant from step 3 for a time sufficient to sterilize the surface.

Major advantages of that process are that it avoids (a) the need for vacuum which is associated with prior art commercial vapour processes, (b) the need for a rinsing step associated with prior art commercial solution processes and (c) the need for temperatures above 60° C. which are damaging to many materials, and (d) it is more effective than prior art nebulant and vapour processes especially when treating occluded, mated and lumen surfaces. In preferred embodiments it uses hydrogen peroxide at concentrations which are not classified as skin irritants and which are safe to transport and handle (unlike commercial vapour and plasma processes which use corrosive and irritating 60% peroxide solutions requiring special packaging and handling precautions). The prior art is comprehensively discussed in our co-pending application.

We have now discovered that at least some of the benefits produced by the method of our co-pending application can be achieved simply by alternative means with some surprising additional and unexpected advantages.

Any discussion of the prior art throughout the specification should in no way be considered as an admission that such prior art is widely known or forms part of common general knowledge in the field.

The present invention arose from the need to find a method to sterilize diagnostic ultrasound ("DU") probes. These instruments are used for a variety of intra cavity procedures including intra rectal, intra vaginal and oesophageal examination and should be sterilized to prevent cross-infection. The instruments are temperature sensitive and cannot be heated above 55-60° C. Several different plastics may be used in their external construction which may involve joined or mated parts. DU Probes have electrical connectors which are sensitive to corrosion. Often procedures are of short duration but sterilization can take much longer than a procedure, therefore a multiplicity of instruments is needed to enable procedures to be undertaken during long sterilization cycles. Each instrument is expensive and the need for multiple instruments adds greatly to the cost of examinations. Moreover, the procedures are often performed in locations where there is no access to centralized or specialized sterilization equipment such as plasma sterilizers which employ high vacuum and cost upwards of $100,000. At present DU probes are commonly disinfected using high level disinfectants such as liquid glutaraldehyde or OPA (ortho phthalyl aldehyde) both of which are associated with a high Occupational Health and Safety risk as well as a risk to patients from residues. Currently no sterilization procedure is available for these instruments and high level disinfection is not considered entirely satisfactory by health professionals using these instruments. It will be understood that the invention is not limited to use for sterilizing DU probes and may be used for disinfecting or sterilizing other articles or surfaces. Furthermore, DU probes are not generally stored in a sterile environment and best practice requires that in such cases they be re-disinfected immediately prior to use.

Cummins U.S. Pat. No. 4,744,951 describes a process in which hydrogen peroxide is vapourized and concentrated in a first chamber by means of heat and pressure reduction. (eg 0.01 atms) Water vapour is withdrawn in preference to hydrogen peroxide vapour through a vacuum pump. The thus concentrated peroxide vapour is then admitted to an evacuated sterilization chamber in which it is allowed to contact an article to be sterilized. The process suffers from the major disadvantages that are associated with the need for a vacuum system and evacuation.

OBJECTS OF THE INVENTION

It is an object of the invention to provide improved means of disinfecting or sterilizing medical instruments which avoids or ameliorates at least some of the disadvantages of the prior art.

It is an object of preferred embodiments of the invention to provide improved means of disinfection or sterilization suitable for treatment of ultrasound probes, or ultrasound radiology probes without requiring pressure reduction.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

BRIEF STATEMENT OF INVENTION

According to a first aspect the present invention provides a method for disinfecting or sterilizing an article or article part comprising the steps of (1) enclosing the article or article part inside a container having a wall of which at least a part is a semipermeable fabric or membrane;

(2) introducing an amount of vaporizable biocide to the interior of said container;

(3) the semipermeable fabric or membrane being selected to allow the biocide to pass from inside to outside of the container as a vapour at atmospheric pressure and to provide a barrier against entry of micro-organisms;

(4) allowing biocide to exit the container through said membrane while at or above atmospheric pressure; and (5) exposing the article or article part to the biocide for a time sufficient to disinfect or sterilize the article.

For preference the entire process is conducted at atmospheric pressure and sufficient of the biocide is removed so that biocide residue, if any, on said article or article part is at or below acceptable levels.

According to a highly preferred second aspect the present invention provides a method for disinfecting or sterilizing an article or article part comprising the steps of:

(1) enclosing the article or article part inside a container having a wall of which at least a part is a semipermeable fabric or membrane;

(2) introducing a biocide as a nebulant to the interior of said container;

(3) the semipermeable fabric or membrane being selected to allow vapour to pass from inside to outside of the container while providing a barrier against entry of micro-organisms and against exit of nebulant particles;

(4) allowing vapour to exit the container through said membrane at or above atmospheric pressure; and (5) exposing the article or article part to the nebulant for a time sufficient to disinfect or sterilize the article.

According to a third aspect the invention provides a method according to the first or second aspect wherein a fluid is directed to flow adjacent the outside of the membrane to expedite vapour removal from the interior. For preference the fluid is air, more preferably humidity conditioned air.

According to a fourth aspect the invention provides a method according to any one of the preceding aspects wherein the biocide is a solution of hydrogen peroxide in water.

The semipermeable fabric or membrane selected in accordance with the third step of the method may be a woven, or non woven fabric, or it may be a sheet or film or a combination thereof and may be of a single layer or multilayer construction. The term "semipermeable membrane" is used herein where the context permits to include all such fabrics and membranes having the selected properties. The semipermeable membrane may be hydrophobic or hydrophilic in nature.

In the first step of the method the article to be sterilized is enclosed in a container having a wall of which at least part is a semipermeable membrane. In some cases the whole article does not require to be sterilized and it is sufficient to enclose that part of the article which requires treatment. By "enclosing" is meant that the article or at least the part to be disinfected is enclosed in the container in such a way that after sterilization (which takes place within the container) no micro-organisms can enter the container or contact the enclosed portion of the article while it remains enclosed. It will be understood that while the invention is capable of use for sterilization (i.e. achieving a log 6 reduction in spores), it can be used with advantage to attain a lower standards of disinfection.

The container may be a rigid or semirigid chamber constructed from, or having openings covered by, the semipermeable membrane or may be a chamber, bag or pouch formed from the semipermeable membrane.

In the second step a biocide is introduced into the interior of the container. In preferred embodiments the biocide is a solution of hydrogen peroxide which is nebulised, and the nebulant then introduced to the container interior. In a highly preferred embodiment a peroxide solution having an initial concentration of at least 6%, preferably 20%-35%, and more preferably 30%-35%, is nebulised. Preferably the solution is nebulised in an ultrasonic nebuliser operated at 2.4 MHz which generates an aerosol in which particles having a size range distribution of about 1-10 microns are suspended in an air stream. As herein used the term "nebulant" describes droplets of liquid (i.e. finely divided liquid particles) entrained in a gas stream. A system of liquid droplets entrained or suspended in a gas is an "aerosol".

In preferred embodiments the container is provided with sealable means for introducing a fluid whereby the aerosol nebulant may be admitted to the container interior. The sealable means may, for example, be an entry port provided with a closable valve, or with a one way valve permitting fluid entry to the container but preventing fluid exit, or a tube communicating with the interior and capable of being heat sealed, or may be a self sealing septum able to be pierced by a nebulant injection nozzle. By any such means an aerosol outlet from the nebuliser is placed in communication with the enclosure interior via the entry port. However it will be understood that in other embodiments the aerosol may be introduced by being generated within the container interior or within a compartment in communication with the container so that the container may be sealed before the aerosol is formed.

The third step of the method in combination with the fourth allows vapour to permeate out of the chamber through the semipermeable membrane at atmospheric pressure. The semipermeable membrane is selected having regard to the need to provide a barrier to microorganism entry and that requirement ensures that nebulant particles are initially unable to permeate out and concentrate (particles per liter) in the container. Without wishing to be bound by theory, it is believed that as water vapour permeates out of the container through the membrane as hereinafter described, and as air permeates in, water evaporates from the nebulant droplets in order to restore the equilibrium vapour pressure within the container. Continuing evaporation from the droplets results in the peroxide solution in the nebulant becoming more concentrated, and in the droplets shrinking in size. As shown in our co pending application, these smaller more concentrated nebulant particles are significantly more effective as a sterilant than prior art hydrogen peroxide vapour and prior art peroxide nebulant sterilants and processes. Air permeating into the container is sterile by virtue that the membrane is not penetrable by micro-organisms. The article or article part is exposed to the nebulant for sufficient time to disinfect the article to a desired level or sterilize it. The container can be sealed after sufficient nebulant has been introduced into the container. That may take place before or after the article has been fully disinfected or sterilized, and before or after substantially all the water vapour has been removed. In the case in which the inlet is provided with a one way valve the container is sealed in the relevant sense at all times after the article or article part has been enclosed. Eventually the nebulant particles vaporise entirely and pass through the semipermeable membrane, leaving the contents dry and free from harmful residue In highly preferred embodiments of the invention a fluid is allowed to flow adjacent the outside of the membrane to expedite vapour removal from the interior. Preferably the fluid is air, more preferably it is preconditioned air (for example dehumidified air). The air flow provides an "exterior current" which removes molecules permeating to the outside of the membrane, whereby to improve the efficiency of vapour removal from the interior of the container. The term "exterior current" is herein used to denote an air flow on the side of the membrane exterior from the container interior and while the direction of flow will usually be in the opposite direction from that of nebulant into the container i.e. a "counter current", the direction of the flow is not critical and where the context admits the term "exterior current" is not intended to imply any particular direction of flow, and includes a counter current.

According to a fifth aspect the invention provides a process according to any one of the preceding aspects wherein the semipermeable membrane is selected to remove one or more vapours by a process of pervaporation.

Although the invention is herein described with reference to hydrogen peroxide as the biocide, it is envisaged that the invention would be equally applicable when the biocide was another peroxide or peroxy compound, or could be used with other known vaporizable biocides or biocides when dissolved in suitable solvents (which need not be aqueous). Furthermore, although it is highly preferred to introduce the biocide as an aerosol, in less preferred embodiments the biocide can be introduced as a vapour and the vapour subsequently removed at atmospheric pressure by an exterior current of air (or other fluid) adjacent the membrane exterior. Introduction of the biocide as an aerosol is greatly preferred because much higher initial densities of biocide per liter of container can be achieved than with a vapour. Our co-pending application indicates that aerosols according to that invention, which are believed to be the same as or similar to the aerosols produced in this process are more effective than vapour.

In other aspects the invention provides apparatus for conducting the method, containers for use in the method, and compositions formed during use of the method.

According to a sixth aspect the present invention provides a method for disinfecting or sterilizing an article or article part comprising the steps of (1) enclosing the article or article part inside a first container having a wall of which at least a part is a semipermeable fabric or membrane;

(2) the semipermeable fabric or membrane being selected to allow vapour to pass from inside to outside of the container while providing a barrier against entry of micro-organisms and against exit of nebulant particles;

(3) admitting a biocide solution comprising a biocide dissolved in a solvent to a second container;

(4) concentrating the biocide in the second container by removal of solvent at atmospheric pressure, to form a concentrated biocide (5) introducing the concentrated biocide as a liquid or a vapour or a combination thereof from the second container to the first; and And wherein steps (3)-(5) are conducted at or about atmospheric pressure.

In preferred embodiments according to the sixth aspect the invention is conducted in a manner similar to that described by Cummins but differs in that a hydrogen peroxide solution in water of for example 35% concentration is firstly concentrated as a nebulant in one chamber by removal of water through a membrane at atmospheric pressure. The concentrated nebulant is then admitted to another chamber which is desirably a bag or other container having a semipermeable membrane as defined as a wall or part thereof which is then sealed. This allows the article to be sterilized and stored sterile in the second container and permits removal of residual hydrogen peroxide In alternative embodiments of the fifth aspect the concentrated hydrogen peroxide is admitted to the first container as a concentrated vapour.

BRIEF DESCRIPTION OF THE DRAWINGS

The invention will now be more particularly described by way of example only with reference to the accompanying drawings wherein:

FIG. 1 is a schematic diagram in vertical cross-section (not to scale) of a first embodiment of a container for use in the invention.

FIG. 2 is a schematic diagram showing a flow sheet of an embodiment of a method of the invention employing a container according to the first embodiment.

FIG. 3 is a schematic diagram showing a flow sheet of a more sophisticated embodiment than that of FIG. 2 of a method of the invention employing a container according to the first embodiment.

FIG. 4 is a schematic diagram in vertical cross-section (not to scale) of a second embodiment of a container for use in the invention.

FIG. 5 (*a*) is a schematic diagram in vertical cross-section (not to scale) showing a third embodiment of a container for use in the invention. and FIG. 5 (*b*) is a schematic diagram showing how the embodiment illustrated in 5 (*a*) may be sealed around an article part.

FIG. 6 illustrates conceptually a sterilizing unit adapted to cooperate with a container such as illustrated in FIGS. 5*a* & *b*. in an open configuration.

FIG. 7 illustrates the apparatus of FIG. 7 in a closed configuration

FIG. 8 shows data in graphical form from example 1 which uses a TYVEK membrane.

FIG. 9 shows data in graphical form from example 3 which uses a KIMGUARD membrane.

FIGS. 10, 11 show data in graphical form from example 5 which shows how the concentration of water and peroxide, respectively, in the container decrease as a function of time and exterior current flow.

FIG. 12 shows data in graphical form from example 6 and illustrates the decline in peroxide concentration in the container as a function of time and counter current air humidity FIG. 13 shows data in graphical form from example 6 and illustrates the decline in peroxide concentration in the container as a function of time and peroxide concentration.

The same numerals are used to identify parts in one drawing having a function corresponding to the same part in another.

DESCRIPTION OF PREFERRED EMBODIMENTS

With reference to FIG. 1 there is shown a first embodiment of a container 1 for use in the invention. In this embodiment container 1 is in the form of a cylindrical cassette or chamber shown schematically in vertical cross section, but the container could be rectangular, any other suitable shape, or formless. In the present example container 1 has a floor 3, a cylindrical wall 4, and a removable lid 5 which may be sealingly attached to container 1, for example by inter engageable screw threaded attachment 7 and an intermediate seal 6 Seal 6 may be a ring in the case of a cylindrical chamber. Lid 5 is removable so that an article 2 to be sterilized can be placed in, or removed from, container 1. Article 2 is supported above the floor of the chamber by a perforated plate or gauze 10 which preferably provides support for article 2 at contact points of minimal mated surface area.

In the present embodiment removable lid 5 has a large opening 8 which is covered by a semi permeable membrane 9 sealed at its edges with the lid by means not illustrated in the drawing. By way of example, membrane 9 may be joined with lid 5 by an adhesive or may be removably sealed over the opening and clamped in place by a frame with suitable seals or the like. If desired the membrane may be supported by an open mesh grid or perforated plate (not illustrated) to provide physical support. Lid 5 with semipermeable membrane 9 constitutes an upper wall of the container. Desirably, the arrangement is such as to provide a substantial area of container 1 wall which is semipermeable. Indicatively, in one example, container 1 has a volume of aprox. 5 liters and opening 8 has an area of about 450 sq. cm of semipermeable membrane.

Semi permeable membrane 9 in the present example is made of KIMGUARD, a three layer non linting laminate fabric having an inner layer which is hydrophobic and resistant to bacterial penetration. The two outer layers provide abrasion resistance and strength. The fabric is permeable by virtue of microscopic channels which provide a tortuous path limiting passage of particles to those of less than 0.2 micron. This fabric allows water and hydrogen peroxide vapours to permeate through the channels of the fabric. The channels do not permit passage of bacteria into the chamber and do not permit nebulant to pass out. Other fabrics and membranes which are permeable by water vapour and hydrogen peroxide vapours and impenetrable by bacteria may be used, for example TYVEK. However we have found that KIMGUARD is 2-3 times more permeable to hydrogen peroxide vapour than TYVEK under the conditions in which we use it. As will be discussed hereinafter other semipermeable membrane materials such as NAFION (which is hydrophilic) and the like may also be employed.

In the present embodiment a tubular inlet 13 communicates with the interior of container 1 via inlet valve 11 which is able to seal the enclosure. Upstream of inlet valve the present example has a connector 12.

Figure 2:
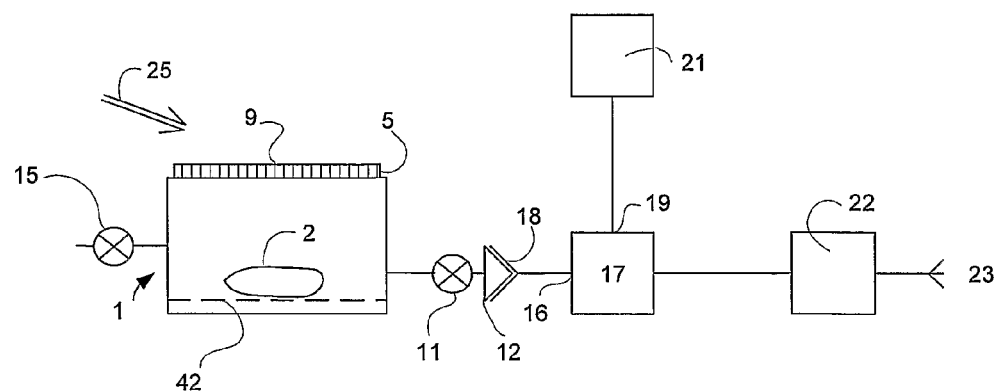

With reference to FIG. 2, there is shown a flowchart schematically illustrating the method of the invention. Lid 5 of container 1 is removed, an article 2 to be sterilized is enclosed interior of container 1, and the lid replaced sealing the article inside. Inlet valve 11 of container 1 is placed in communication with aerosol outlet 16 of a nebuliser 17 via a connector 18 adapted for connection with connector 12 of container 1. Nebuliser 17 is, for example, a nebulizer such as described in our co pending application with reference to FIGS. 3 & 4 thereof and driven at 2.4 MHz and has a liquid inlet 19, an air inlet 20 as well as nebulant outlet 16. A solution of hydrogen peroxide in water at a concentration of, for example, 35% is fed from a reservoir 21 via liquid inlet 19 to nebuliser 17 which receives air at its air inlet 20 from a fan or blower 22 which draws air from the atmosphere at 23. This air is not necessarily sterile, but is desirably filtered, and if preferred could be sterilized, for example, by a hepafilter. The 35% hydrogen peroxide solution is nebulised in the air stream by nebuliser 17 which produces an aerosol in which finely divided particles or droplets of 35% hydrogen peroxide solution are suspended as a nebulant and which flows out of the nebuliser at aerosol outlet 16. Typically, more than 90% of hydrogen peroxide droplets in the nebulant emanating at outlet 16 are in the 1-10 micron range with the median size at around 3-5 microns ("micro particles")

With valve 11 open, aerosol from nebuliser 17 is propelled into the interior of container 1 by fan 22. The micron range droplets of hydrogen peroxide have a large air/liquid interface and at ambient or low (below 60° C.) temperatures and atmospheric pressure water has a much higher vapour pressure than hydrogen peroxide and evaporates from the droplet surface in preference to hydrogen peroxide. This water vapour is able to permeate through the semi permeable fabric 9 and does so with surprising speed. Water vapour removal can be facilitated by blowing a stream 25 of "exterior current" air over the external surface of the semi permeable membrane. The exterior current air stream removes water molecules reaching the exterior surface of membrane 9 and facilitates permeation from within container 1. As water vapour leaves the chamber, more water evaporates from the surface of liquid droplets in order to restore the partial pressure of water in the vapour phase in equilibrium with the liquid in the nebulant droplets.

The aerosol entering container 1 is unable to escape from the container because the particle size is large in comparison with the membrane pore size. The liquid particles become more concentrated as water vapour is removed, and as more evaporates from the droplets, the concentration in the droplets approaching 60%, or upwards, of hydrogen peroxide concentration. The droplets also reduce in diameter. As the nebulant droplets become smaller their diffusion coefficient increases exponentially. In our co pending application we have shown that these more concentrated, smaller, particles in the presence of water at relative humidities below about 80%, and preferably below 60% are not only effective in sterilizing open exposed surfaces in a remarkably short time but also are able to penetrate between mated surfaces which is important for sterilizing instruments at points of support, or in the case of lumens at points of connection (if any). In contrast to the method described in our co pending application the nebulant need not in this invention be subjected to energy of a kind and for a duration sufficient to vaporize solvent in preference to sterilizing agent, whereby to increase the concentration of the agent in the nebulant particles. Permeation through semipermeable membrane 9 achieves a similar result, also without the use of vacuum, but in this case without the expenditure of as much energy.

Whilst concentrations of peroxide in droplets produced from 30-35% peroxide solution typically approach 60% or upwards, it is not always necessary that such a high peroxide concentration is achieved. For example, in other preferred embodiments, a starting solution which has a concentration of 10 to 15% peroxide can be nebulised and concentrated to around 45 to 60% peroxide. Any starting concentration of peroxide can be used, and concentrated to any level up to the theoretical maximum achievable under the prevailing conditions of relative humidity and temperature. Generally, in practical terms, a peroxide concentration of 10-15% to 30-35% is employed as the starting solution, which is concentrated up to 45-60% or above in the nebulant.

The nebulant may be introduced into container 1 continuously or intermittently, for example, 2 secs on/18 secs off; or 5 secs on/15 secs off; over a period of, for example, 2 minutes. Container 1 may then be isolated from the nebuliser by closing valve 11. Removal of vapour from the container through semipermeable membrane 9 may be continued. As the concentration of hydrogen peroxide in the droplets increases, the proportion of hydrogen peroxide in the vapour in equilibrium with the droplets increases. Any peroxide vapour which vapourises also permeates out of the chamber through the semipermeable membrane 9, and is removed in the exterior flowing air. Eventually the aerosol droplets within container 1 diminish in size to a point where they either become so small that they are able to permeate membrane 9, or vaporise completely and permeate the membrane as molecules. Sterile air, as filtered by the membrane, permeates into the chamber as water vapour permeates out.

At the completion of the exemplified two minute cycle, container 1 is isolated from nebuliser 17 by means of valve 11 (or if a non return valve is used the nebuliser may be switched off) and the exterior flow of air continued for a further period, for example, 8 mins. Container 1 may then be disconnected at connector 12 and removed for storage of the sterile article until required. After removal of sterile article 2 for use, container 1 may be reused.

In preferred embodiments the permeation is continued until substantially all the remaining hydrogen peroxide in the container has evaporated and permeated out. (By "substantially all" in this context is meant that remaining peroxide has been reduced to a residue level that is considered acceptable. Thus remaining peroxide has vaporised and has a concentration of below about 100 ppm, at which level the amount of peroxide that is condensed on surfaces will be at a concentration of below about 1 microgram/sq. cm.)

In less preferred embodiments a source of air, for example sterile warm dry air may be blown into container 1 via inlet valve 11 (by means not illustrated in FIG. 2) to expedite peroxide removal and drying of article 2 prior to sealing the container. This drying air can be allowed to pass out through the semipermeable membrane or there can optionally be provided a second outlet 15 provided with a valve or non return valve or the like to allow a higher flow rate of drying air into through and out of the apparatus. However it will be appreciated that a major advantage of using an exterior current air on the outside of the membrane to remove residual water and peroxide is that the exterior current air does not need to be sterile, while air used to dry from the inside would need to be sterile, e.g. filtered through a hepafilter. For preference the exterior current air (and any air streams containing hydrogen peroxide) is fed through a catalytic destructor to render the peroxide harmless before it is vented, or through a recovery unit which enables it to be recovered for reuse. In each case valve 11 is closed prior to completion of the sterilization.

Figure 3:
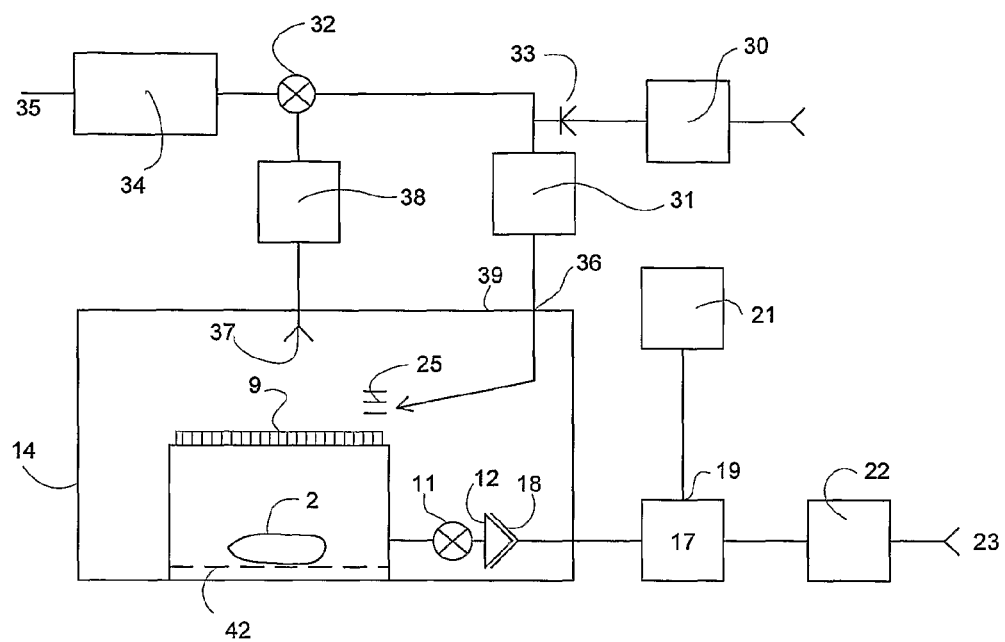

With reference to FIG. 3 there is shown a more sophisticated flow diagram for conducting a method according to the invention. This apparatus includes parts described with reference to FIG. 2 and those parts perform the same function as previously described. In the embodiment illustrated in FIG. 3 container 1 enclosing article 2 is placed within a larger outer chamber 14 having a removable lid 39 or other access means such as a door. Nebulant is delivered from nebuliser 17 to container 1 in the manner previously described, the feed line penetrating the wall of outer chamber 14. Air from the atmosphere is drawn in by fan or blower 30, conditioned by conventional means (for example heated to 45° C., and having water removed to 20% RH) in a unit 31 and conducted into outer chamber 14 at 36 and then directed tangentially as a fluid flow 25 adjacent the surface of semipermeable fabric 9 external to container 1. This exterior current air flow exits from outer chamber 14 at 37 and is then either optionally directed by valve 32 and non-return valve 33 to be recirculated through conditioner 31, or to be treated in a catalytic destructor 34 (desirable, but not essential) and vented at 35. An additional fan such as 38 may optionally be provided on the outlet side 37 of chamber 14.

In a preferred variation of the embodiments described above a NAFION membrane is substituted for the KIMGUARD fabric previously described as used for semipermeable membrane 9. NAFION is a copolymer of tetrafluoroethylene and perfluoro-3,6-dioxa-4-methyl-octene-sulfonic acid. Such materials are hydrophilic and have a very high water of hydration. NAFION is able to absorb 22% by weight of water. In this variation the absorption proceeds as a first order kinetic reaction. Water molecules pass through the membrane and then evaporate into the surrounding air until equilibrium with the external humidity is reached in a continuous process called pervaporation. An exterior current flow of air over the external side of the membrane provides rapid removal of the moisture from the outside surface and speeds the pervaporation process. Unlike simple permeation wherein the molecules merely diffuse through the open pores, in pervaporation the membrane is active in selectively drawing molecules from one side of the membrane to the other, and may do so at differential rates for differing types of chemical molecule.

In this specification where the context permits references to a semi permeable fabric or membrane include fabrics or membranes suitable for pervaporation as well those only suitable for simple permeation, and references to permeation include references to pervaporation. Other membranes than those described and membranes may be used and may include membranes suitable for pervaporation.

Figure 4:
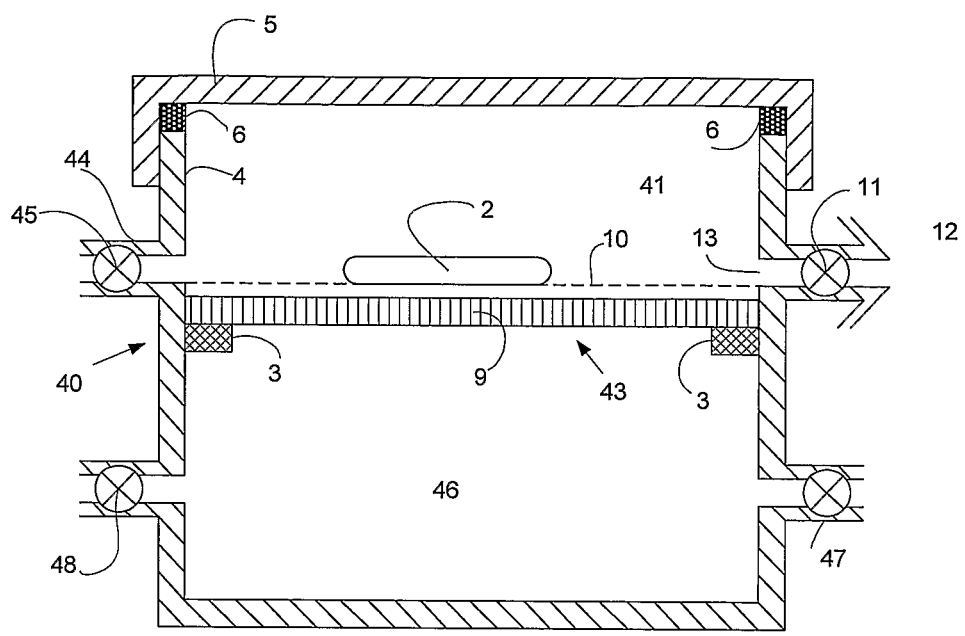

A second embodiment of a container for use in the invention is illustrated schematically in FIG. 4 in which there is provided a cassette 40 which is divided into two chambers by a semipermeable membrane partition 9. The partition may be supported or reinforced. In the present example the upper chamber 41 is the sterilization enclosure which corresponds in function to container 1 and has walls 4, a floor 3 and a lid 5 which is removable to enable an article 2 to be sealed in the upper chamber. Article 2 is supported on an open mesh gauze or grid 10. A seal 6 between lid 5 and the interior prevents ingress of bacteria when the lid is in its sealed closed configuration. Lid 5 may be held in place in sealing engagement against seal 6 by any suitable means, for example clamps (not illustrated). The floor 3 defines a large opening 43 which penetrates from the upper to the lower chamber and which is covered by a semipermeable membrane or fabric 9 which in the present example is a NAFION membrane. Upper chamber 41 of the cassette has a tubular inlet 13 with a valve 11 and connector 12 and optionally has an outlet tube 44 with valve 45.

Lower chamber 46 has an inlet 47 connectable to a source of exterior current air which is preferably associated with means (heaters condensers or the like) to precondition it with respect to temperature and relative humidity and an air outlet 48.

In use this embodiment can be connected into a circuit similar to that previously described with reference to FIG. 2. The interior of upper chamber 41 may be connected to nebuliser 17 via aerosol inlet tube 9 and valve 10 in a similar manner to the container of FIG. 1. Outlet 45 if present would be closed. The aerosol is unable to pass out of the upper chamber 41 through membrane 9 and high concentrations densities of peroxide nebulant can be built up within chamber 41. When the concentration is sufficiently high, chamber 41 may be sealed. Lower compartment 46 air inlet 47 is connected to the air source of FIG. 2 at 36, while lower chamber outlet would be connected to the circuit of FIG. 2 at 37. The lower chamber 46 thus performs the function that in FIG. 2 was performed by larger chamber 14. An current of air flowing into lower chamber 46 at inlet 47 through lower chamber 46 and over the surface of the NAFION membrane (exterior to upper chamber 41) and out via outlet 48 speedily removes vapour from lower chamber 46 and that in turn speeds permeation of vapour out of upper chamber 41. As water vapour is removed, the peroxide solution nebulant particles in chamber 41 become more concentrated and smaller As the process continues eventually all the aerosol consists of very concentrated peroxide solution, the peroxide vapourises, still at atmospheric pressure, at a rate similar to the peroxide removal rate, until no aerosol remains and a the article is dry and sterile. As previously discussed, after sufficient aerosol has been admitted and sufficient time has elapsed to achieve a desired rate of disinfection/sterilization, warm air, dry air, or warm dry air may be allowed to circulate into, through and out of the upper chamber to speed reduction of residual peroxide, if any, to acceptable levels.

Figure 5:
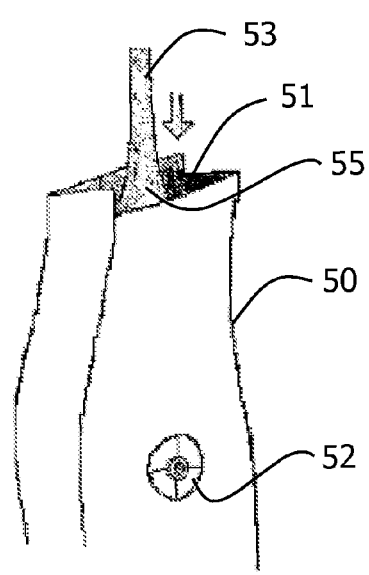
Figure 5:
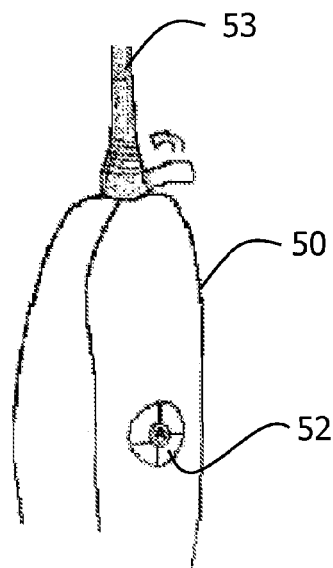

A highly preferred third embodiment will now be described with reference to FIG. 5a and 5b In this embodiment of a container for use in the invention, the container is a bag 50 formed from a semipermeable membrane. The bag is desirably supplied open at one end 51 so that an article can be inserted inside it. In the present example the article to be disinfected is an ultrasound radiology probe 55 having a long cable 53 with an electrical connector at the cable end remote from the probe. In such case it may be sufficient to place the probe part requiring sterilization in the bag and to leave the probe's connecting cable and electrical connector (or at least that portion of it which is not required to be sterile) extending out of the bag. Only a small portion of the cable joining the probe is shown in the drawings. Once the article part is placed in bag 50 the open end 51 can be sealed by any suitable means. In the present example, the open neck is wrapped around the cable and taped in such a way as to seal the probe in the bag interior as shown in the sequence of FIG. 5a and 5b. In the case in which an article may be placed entirely within a bag the neck of the bag can be closed for example by heat sealing or rolling the end and clamping the roll, by use of removable sealants or putties, or other suitable means to prevent bacteria penetrating bag 50 after sterilization and before reopening. It will be understood that the bag 50 need not be made entirely of semipermeable membrane and may include one or more panels of other suitable materials such as a strong transparent impermeable clear film.

Bag 50 may be any suitable shape and may be reinforced to maintain a shape, or may include a removable skeletal structure to assist in shape maintenance and handling, or may be formless. Desirably, the bag is provided with an integral aerosol entry port 52 by means of which it can be attached to a nebuliser output such as 16 in FIG. 2, the port being fitted with a non return valve so that aerosol or fluid may only flow towards the interior of the bag, or may have a self sealing portion through which an injection spigot can penetrate. Port 52 may be provided with a protective closure or cap.

Figure 6:
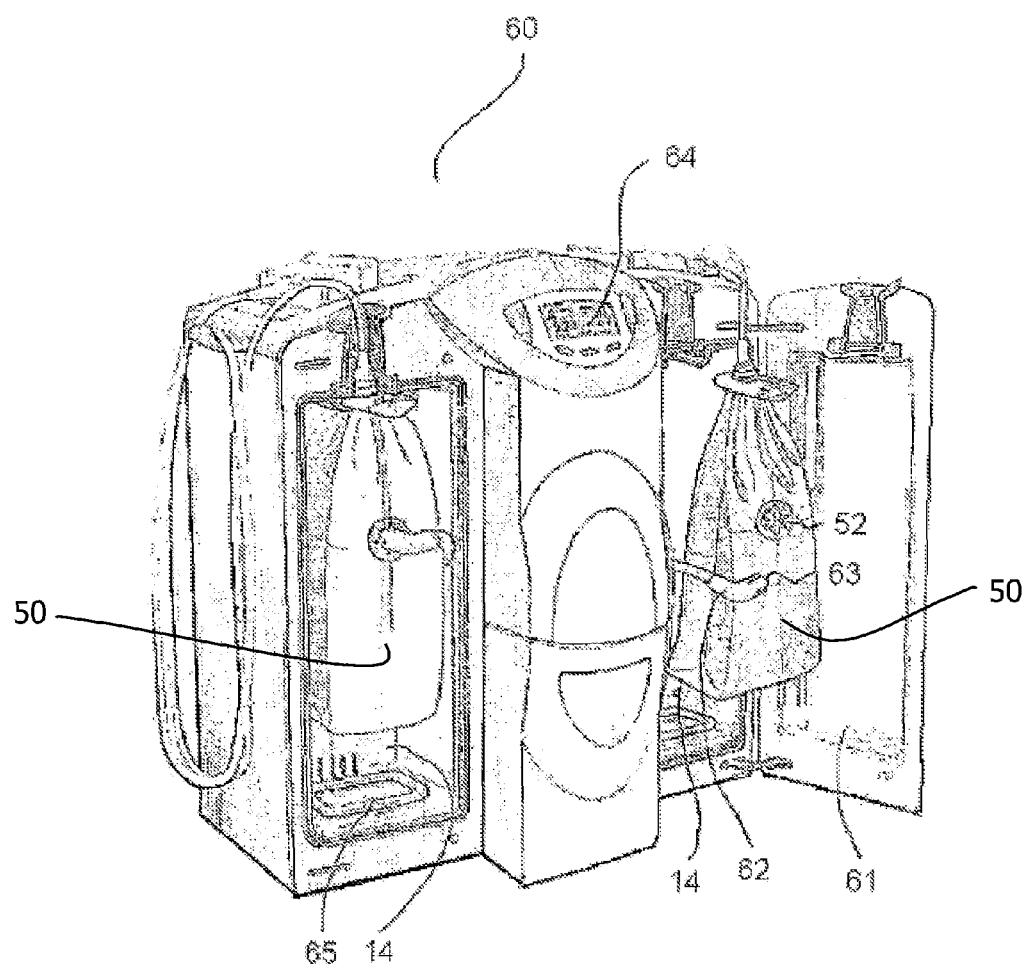
Figure 7:
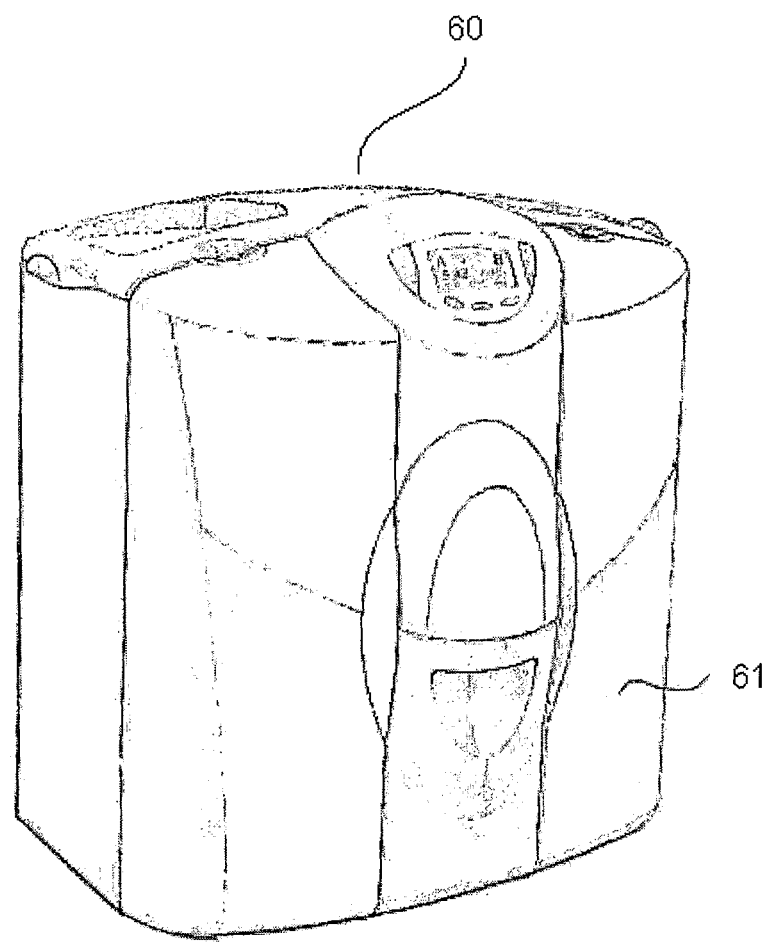

In this embodiment, bag 50 containing the article sealed within it, or the article part to be sterilized sealed within it, is placed in a console 60 shown conceptually in FIGS. 6, 7 provided with means adapted to connect the integral bag port with a source of aerosol. The unit illustrated in FIGS. 6, 7 is adapted to sterilize two bags 50 at a time, but units could be designed for one or any other number of bags.

As shown in FIG. 6, console 60 has two chambers 14 in which bags 50 can be suspended and which can be closed by means of hinged doors 61 or the like. Console 60 includes a nebuliser 17, (not visible in FIG. 6) the aerosol outlet 16 (not visible in FIG. 6) of which is connectable by means of a hose 62 and connector 63 to connect inter-engageably with inlet port 52 of bags 50. Doors 61 (of which only one is illustrated in FIG. 6) can then be shut to surround bags 50.

Circuits electrically connected with control panel 64 of console 60 provide for nebuliser 17 to be energised according to a selected programme whereby an aerosol containing e.g. 35% hydrogen peroxide as the nebulant is delivered into bag 50 via hose 62 and connector 63 at a predetermined rate and duration (eg intermittently; e.g. 2 secs on 5 secs off; for a period of eg 2 minutes). Console 60 and hinged door shell 61 cooperate to provide an insulated environment surrounding connected bag 50 and corresponding in function to outer chamber 14 of FIG. 3 Control panel 64 also provides for circulation of exterior current air over the exterior surface of bag 50 to remove water vapour and hydrogen peroxide vapour permeating out. For example air could be drawn from the back of the unit by a fan, passed over a heating element 65 and is constrained by the design of the chamber to flow over the bag surface. The air might then be vented at the top (if the unit is designed for operation in a fume cabinet) or directed through a catalytic peroxide destructor prior to venting (not visible in the drawing). FIG. 7 shows the conceptual unit of FIG. 6 with doors closed.

Example 1

A chamber similar to that shown in FIG. 1 but of rectangular form was provided with a membrane of TYVEK fabric, the chamber having a volume of 0.5 liters and the membrane having an area of 110 cm². The chamber was placed in outer chamber 14 of the circuit of FIG. 3 which was operated under the following conditions:

| | |
|---|---|
| Initial Hydrogen Peroxide concentration: | 35% |
| Cassette temperature: | nominal 50° C., (actual 49.5-51.0° C.) |
| Nebuliser power: | 10 w |
| Rate of nebulisation | 2 g/min |
| Aerosol flow rate | 2 m/s |
| Nebulisation Duration: | 2 minutes |
| Duty cycles | A. 2 secs on/10 secs off |
| | B. 5 secs on/15 secs off |
| | C. 10 secs on and 10 secs off |
| Exterior current flow Air flow rate | 4.5 L/min |

Nebulant was injected into the chamber during two minute nebulisation duration, with the nebuliser being operated according to duty cycle A. At the conclusion of the two minutes the cassette was sealed off, and air passed as a counter current flow over the exterior surface of the membrane for 8 mins (total run 10 mins). During the two minutes of nebulization (nebulant injection) and subsequent 8 minutes the concentration of water vapour and of hydrogen peroxide vapour in the sterilization chamber were monitored. The concentration of water vapour and hydrogen peroxide in the exterior current air were also monitored. (in practice of the invention it may be preferred to run the exterior current flow from an earlier, or later, stage in the cycle).

Figure 8:
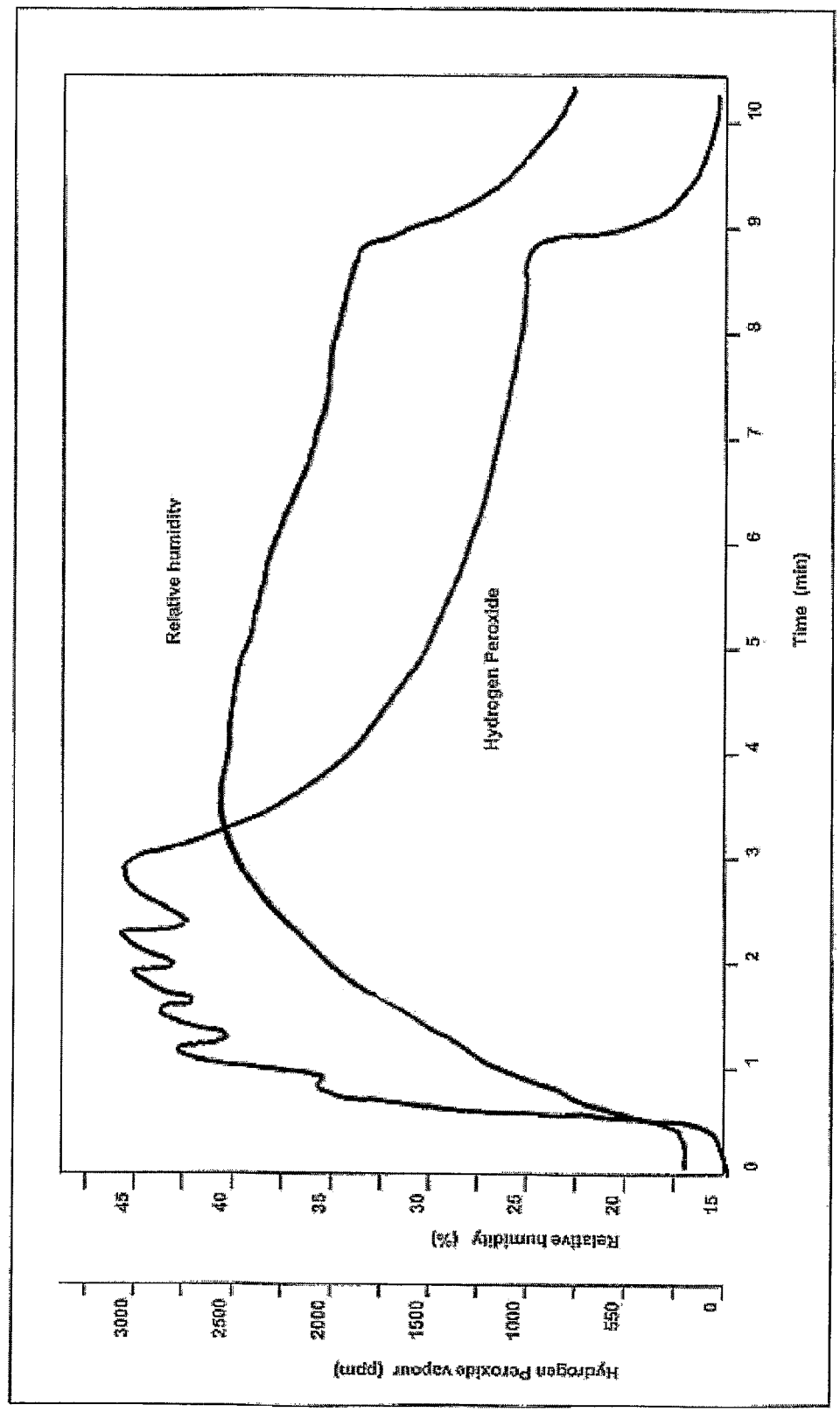

FIG. 8 shows graphically how the concentration of water vapour (expressed as relative humidity) and of hydrogen peroxide vapour (expressed as ppm) varied with time within container 1 over the 10 minute period. Temperature was also monitored and remained at 50° C. with only minor variation throughout.

With reference to FIG. 8 it can be seen that water vapour concentration rapidly climbs reaching about 40% humidity (within about 3.5 min), and thereafter declines to about 9 minutes, then falling sharply. The hydrogen peroxide vapour also peaks quickly at slightly above 3000 ppm within container 1 within about the first three minutes (by which time nebulisation has ceased), and thereafter declines almost exponentially to 9 minutes then dropping sharply at about 9 minutes to less than about 100 ppm. It is believed that the rapid initial rise in both peroxide and water vapour concentrations indicates a rapid equilibration between the partial pressure of water vapour in the container with the water in the nebulant, the peaks being due to the peroxide concentration reaching the point where peroxide and water evaporate at a constant ratio, and the decline being due to removal of diminishing amounts of water remaining within the chamber. After 10 minutes, less than 1 microgram/cm² could be detected on the surface of articles taken from the chamber.

Broadly similar results were obtained with duty cycles B and C but longer water removal periods were required.

Example 2

Example 1 was repeated but using a flow rate of exterior current air of 12.0 L/min. The results were broadly similar in terms of the profile seen, but both water and peroxide removal occur much more quickly, peroxide being substantially removed within about 7 minutes.

Example 3

Figure 9:
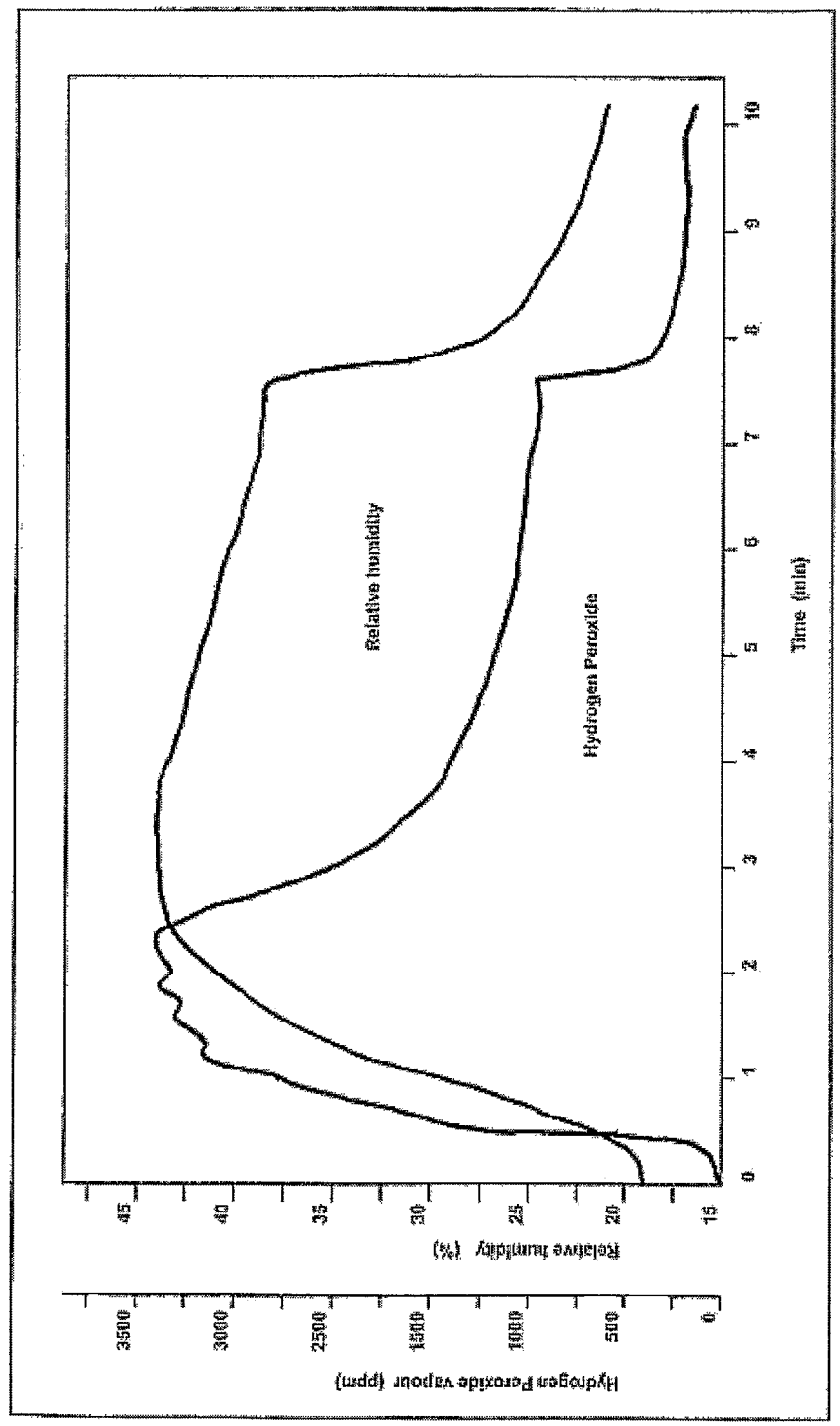

In this example the procedure of example 1 was repeated under the same conditions as in example 1 except that the TYVEK membrane 9 was replaced with a KIMGUARD membrane 9. The results are shown in FIG. 9.

Example 4

In this example the procedure of example 1 was repeated under the same conditions as in example 1 except that the TYVEK membrane 9 was replaced with a NAFION membrane. The results obtained were broadly similar to those obtained with TYVEK and KIMGUARD.

Example 5

Figure 10:
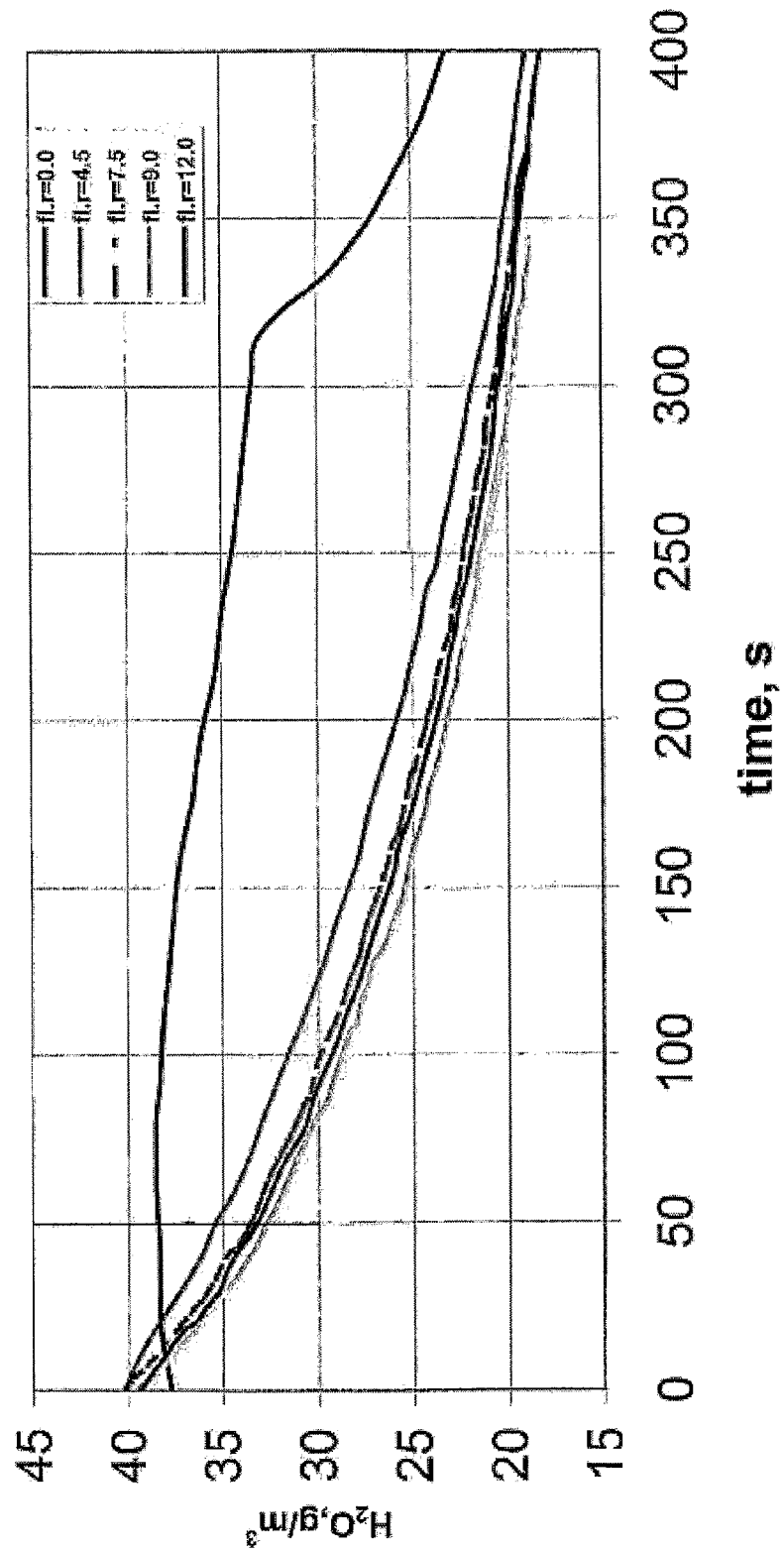

FIG. 10 shows how the extraction rate of water vapour from the container changes over time for different exterior current air flow rates. In this example a KIMGUARD membrane 9 was used in conditions as in example 1. The faster the exterior current air flows, the more rapidly water is removed—but this is subject to the law of declining returns. While there was a significant benefit in increasing air flow from 0 to 4.5 m/sec there was less additional benefit in going from 4.5 to 9.0 m/s and even less benefit in going from 9.0 to 12.0 m/s.

Figure 11:
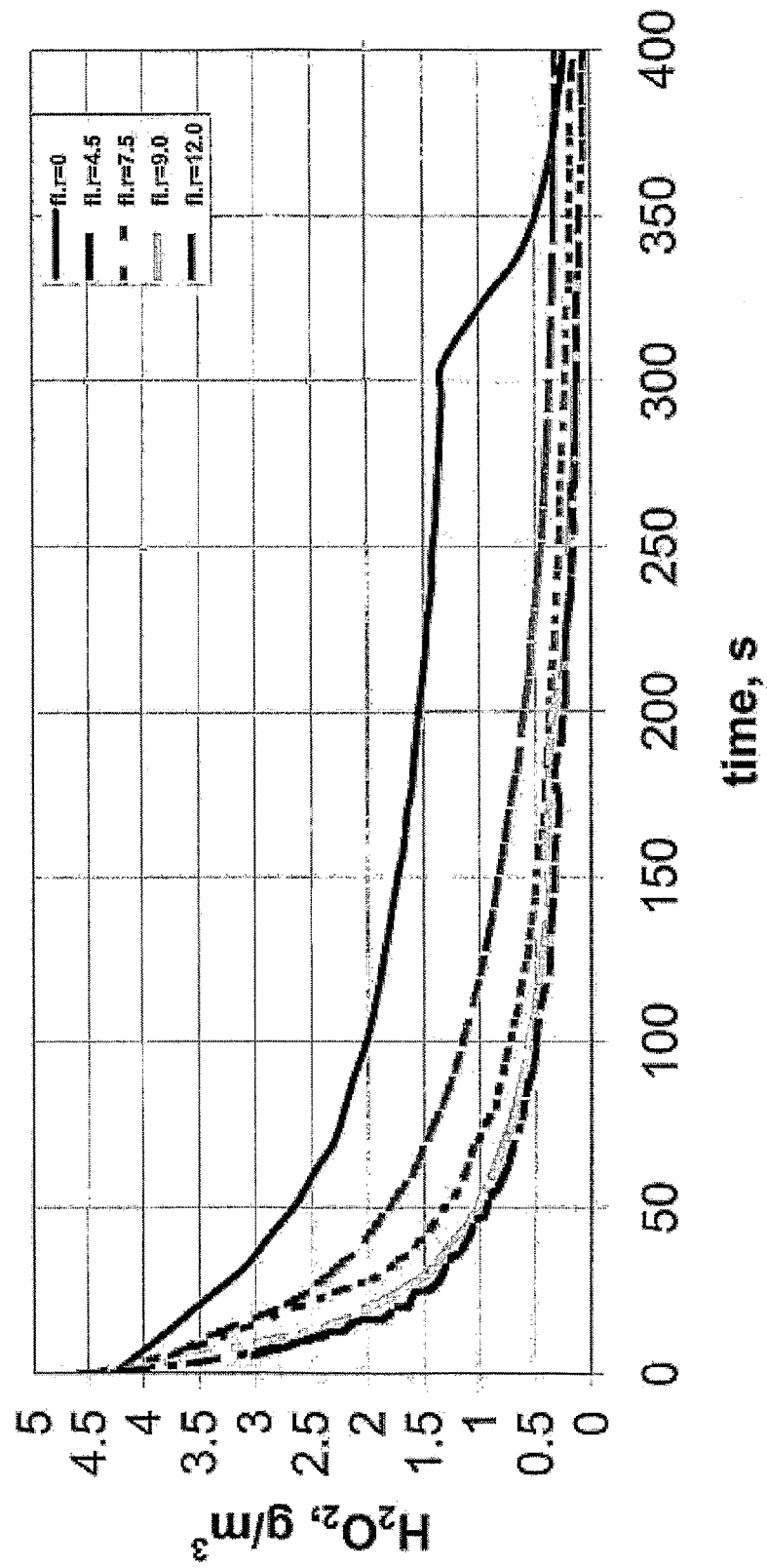

FIG. 11 shows the corresponding effect on hydrogen peroxide extraction rate (initial concentration 35%). The amount of Hydrogen peroxide declines rapidly, and the removal is considerably enhanced by air flow, but the benefit of increasing airflow rate above 4.5 m/s is small and above 7.5 m/s is marginal. Broadly similar results were obtained with membranes of TYVEK or NAFION.

Example 6

Figure 12:
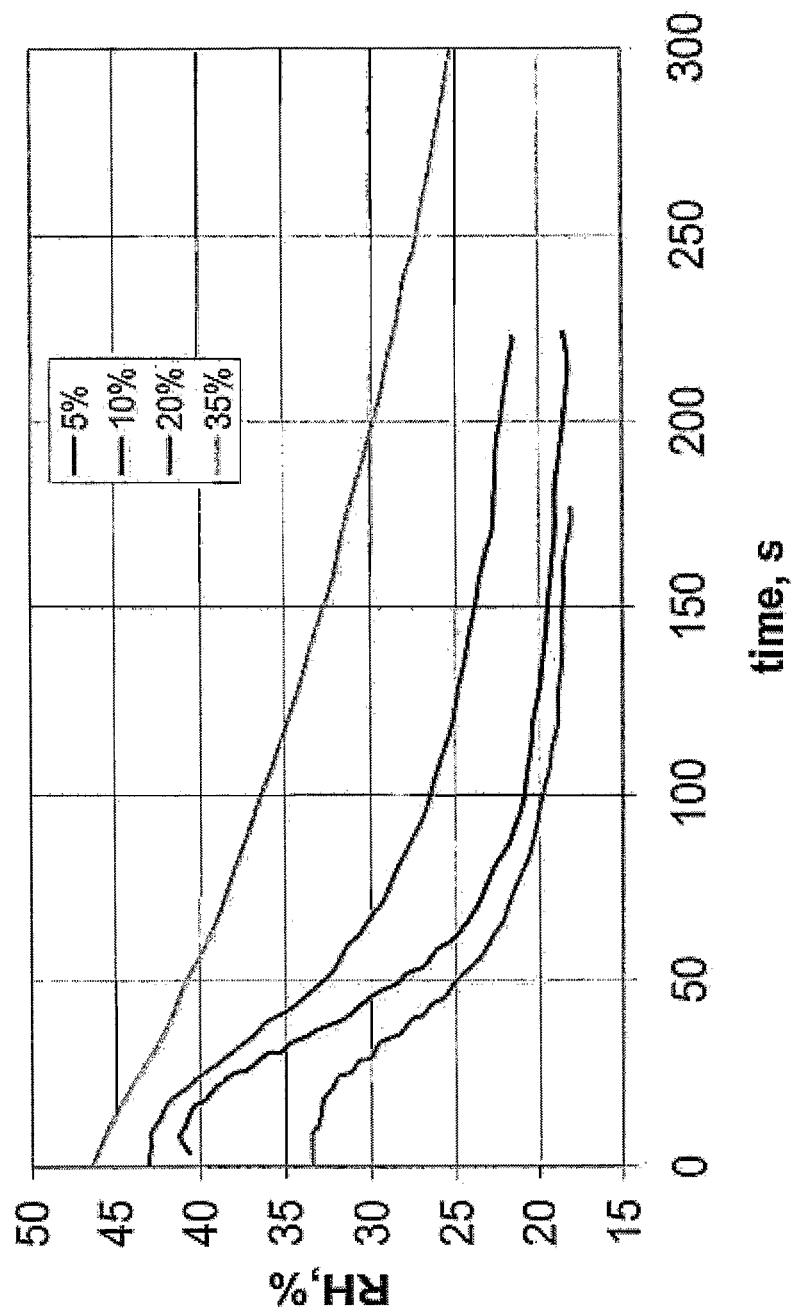
Figure 13:
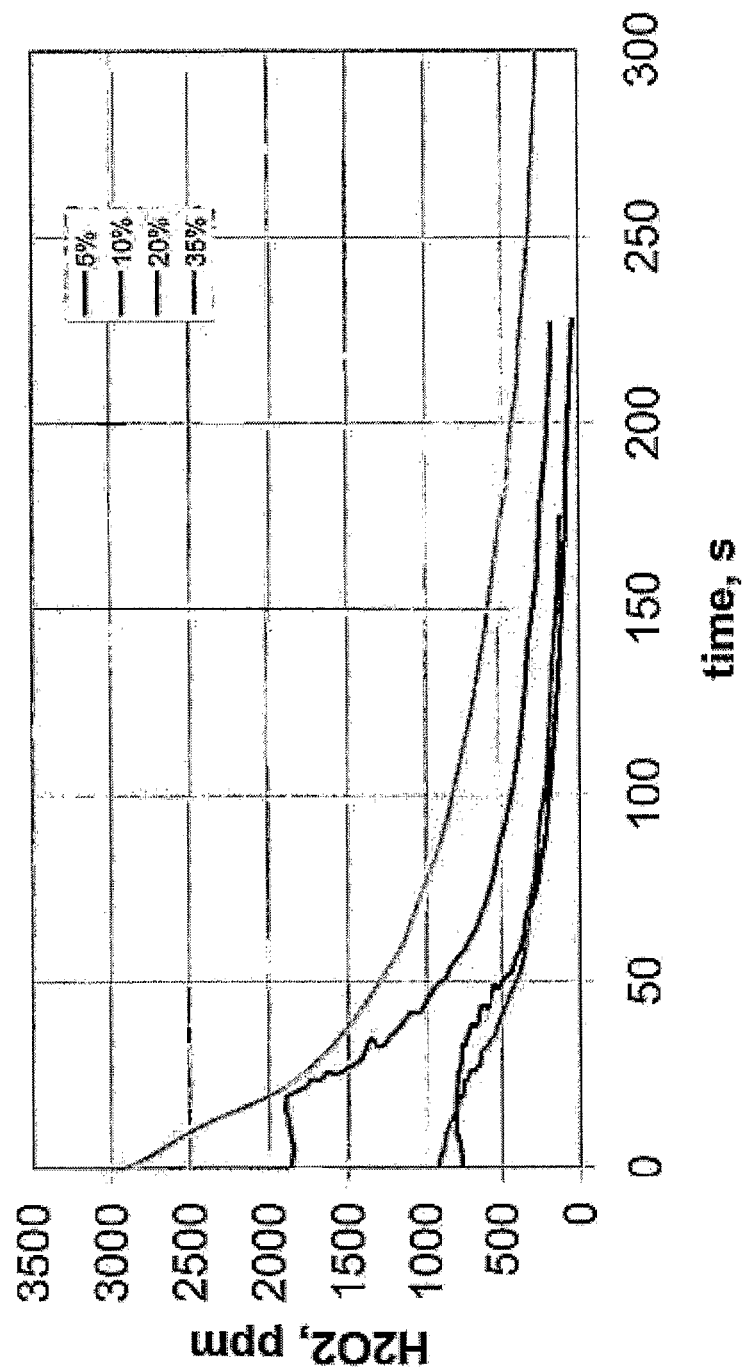

Example 1 was repeated using KIMGUARD as the membrane fabric, but varying the concentration of hydrogen peroxide solution fed to the nebuliser. The flow rate of the exterior current air was 3 m/sec. The effect on RH % and of peroxide concentration in container 1 as a function of time is shown in FIGS. 12 and 13 respectively. Hydrogen peroxide solution of 35% or less would not be classified as skin irritants in rabbits by EU criteria (ECETOC, 1996), and is able to be handled without special precautions. FIGS. 12,13 show that an initial concentrations of peroxide below 20% can also be used, but at the cost of somewhat longer removal times.

Example 7

The particle size of nebulant in an aerosol emanating from port 45 when membrane 9 was a KIMGUARD semipermeable membrane was compared with the particle size when membrane 9 was NAFION. It was found that the particle size distribution shifts towards smaller particles as a function of exterior flow rate of air on the exterior of the semipermeable membrane.

Tables 1 to 4 exemplify the effect. Table 1 shows the particle size distribution of a nebulant from an ultrasonic nebuliser fed with 30% hydrogen peroxide solution at various temperatures.

TABLE 1

| Heater's outlet T ° C. | 10% below (particle size, μm) | 50% below (particle size, μm) | 90% below (particle size, μm) |
|---|---|---|---|
| 25 | 2.84 | 5.5 | 9.48 |
| 55 | 0.95 | 1.36 | 2.0 |
| 60 | 0.58 | 0.86 | 1.36 |

Table 2 shows the particle size data of the nebulant when a NAFION membrane was used with various airflow rates on the exterior side.

TABLE 2

| Counter flow m/s | 10% below (particle size, μm) | 50% below (particle size, μm) | 90% below (particle size, μm) |
|---|---|---|---|
| 0 | 2.29 | 4.61 | 8.58 |
| 3.2 | 2.33 | 3.99 | 6.36 |
| 7.5 | 2.0 | 2.9 | 3.96 |

Table 3 shows the particle size data of the nebulant when a KIMGUARD membrane was used at various flow air flow rates on the exterior side.

TABLE 3

| Counter flow m/s | 10% below (particle size, μm) | 50% below (particle size, μm) | 90% below (particle size, μm) |
|---|---|---|---|
| 0 | 2.29 | 4.61 | 8.58 |
| 3.2 | 2.31 | 4.17 | 7.2 |
| 7.5 | 2.57 | 4.2 | 6.51 |

Example 8

Table 4 illustrates the biocidal efficacy of the system using a KIMGUARD bag as the container. Microbiology was as described in our co-pending application. The bag had a surface area of 644 sq. cm. Air of RH=20% was blown over the bag exterior at 12 m/s throughout the exposure time. A Log 6 reduction in bio burden was obtained in within 5 minutes nebulising a 10% peroxide solution and within 2 minutes nebulising a 30% peroxide solution. Residuals peroxide concentrations at the conclusion were below 250 ppm. Residuals on the surface of the article were below 1 microgram per sq. cm.

TABLE 4

| Expt number | Initial $H_2O_2$ Conc. % | Nebulizer function cycle, ON/Off sec | Nebulizer function time mins | Total exposure time mins | Nebulant output g/min | Temp. in bag °C. | Amount of initial solution used (g) | Amount of $H_2O_2$ delivered into the bag (g/L) | $H_2O_2$ vapour in the bag (ppm) at end of nebuliser function time | Relative humidity in the chamber start/end % | Pennicylinders Log reduction of bio burden | Plate count* |
|---|---|---|---|---|---|---|---|---|---|---|---|---|
| A | 10 | 2/18 | 2 | 5 | 2.2 | 40 | 0.54 | 0.0338 | 150 | 15/51 | 6.0 | 0 |
|   |    |     |   |   |     |    |      |        |     |       | 6.0 | 0 |
|   |    |     |   |   |     |    |      |        |     |       | 6.0 | 0 |
| B | 30 | 8/12 | 2 | 2 | 0.9 | 44 | 1.31 | 0.246 | 250 | 25/41 | 6.0 | 0 |
|   |    |     |   |   |     |    |      |        |     |       | 6.0 | 0 |
|   |    |     |   |   |     |    |      |        |     |       | 6.0 | 0 |
| C | 30 | 8/12 | 1 | 2 | 1.4 | 46 | 0.69 | 0.129 | 100 | 49/52 | 6.5 | 0 |
|   |    |     |   |   |     |    |      |        |     |       | 5.0 | 10 |
|   |    |     |   |   |     |    |      |        |     |       | 5.0 | 10 |

Example 9 (Residuals)

Example 2 was repeated with differing duty cycles and using samples of various materials under the conditions shown below. The residual peroxide levels were then measured. Table 5 shows the residual peroxide levels on materials selected to be representative of those commonly found on DU probes. In this example:
Delivery was for 1 min in total.
Exposure time was 2 min
Drying/aeration time 2 min
Total elapsed cycle time was 5 minutes

TABLE 5

| Experiment | Initial Peroxide Concentration (%) | Duty Cycle | Total Peroxide Delivered (g) | Temp. °C. | Material (10 cm$^2$) | Residual Peroxide (µg/cm$^2$) |
|---|---|---|---|---|---|---|
| A | 30 | 5 s on/ 15 s off | 0.081 | 45 | ABS** | 2.0 |
|   |    |     |       |    | Santoprene | 0* |
|   |    |     |       |    | Silicone | 2.3 |
| B | 30 | 8 s on/ 12 s off | 0.165 | 45 | ABS | 5.8 |
|   |    |     |       |    | Santoprene | 0.0* |
|   |    |     |       |    | Silicone | 4 |
|   |    |     |       |    | Stainless steel | 0.0* |
|   |    |     |       |    | glass | 0.0* |

*below detection level of assay
**Acrylonitrile butadiene stryrene.

Although the invention has been herein described with reference to hydrogen peroxide as the sterilizing agent, the invention could use other peroxides, peroxy-compounds, or complexes of either. Other classes of biocide could be used including without limitation halogenated biocides, phenolic biocides and quaternary compound biocides and it may be advantageous to use solvents other than water. Likewise, although the invention has been herein exemplified primarily with reference to starting solutions having 35% peroxide, other starting concentrations can be employed, although concentrations between about 20% and 35% are preferred.

The container having a wall of which at least a part is a semipermeable membrane or fabric may be of any suitable shape and design having regard to the requirements of the process herein described and can be sealed in any manner impenetrable by micro organisms. Other semipermeable membranes or fabrics can be selected based on the teaching herein provided.

The container may be permanently connected to the nebuliser circuit or may be able to be connected and disconnected by a tube and spigot connection, by suitable connectors or other means. The apparatus may be made from any suitable materials and the process may be monitored by instruments which for preference monitor the exterior flow rather than the interior of the container, but may monitor the conditions within the container if desired. The nebuliser need not be ultrasonic, and any other means for forming an aerosol could be used including sprays, jets, and other devices. It is conceivable that peroxide could be prepacked and stored as an aerosol in an aerosol container and could be admitted from the aerosol container. It is also envisaged that cassettes incorporating an ultrasonic transducer could be used to generate an aerosol in situ within the enclosed container which would be provided with electrical connections to the exterior to provide for energisation and control.

Although it is highly preferred to employ an aerosol to conduct the sterilization, the concept of invention would also be applicable to processes in which a predetermined solid or liquid sterilant such as peroxide is admitted to the container as a vapour or as a solid or liquid which is subsequently vaporised. A number of such processes have been describe (for example in U.S. Pat. No. 6,451,254, U.S. Pat. No. 6,673,313, U.S. Pat. No. 6,656,426) all of which require involve concentrating a hydrogen peroxide solution by lowering the pressure to preferentially evaporate water and removing the water through a vacuum pump prior to vaporising the solution. The principles herein taught could be applied to concentrate the peroxide in such vapour processes by permeation or pervaporation through a membrane, without the need for pressure reduction. However the benefits (described in our co-pending application) of utilizing the aerosol of the invention would be lost as a sterilant would be lost.

If a lumen or device such as an endoscope having one or more lumens is to be treated, the aerosol may be directed through the lumen as well as around its exterior and for that purpose suitable connections or manifolds may be provided for example in chamber 41 of the cassette of FIG. 4.

Although the process has been herein described and exemplified with reference to examples wherein the whole process is conducted in one container, it will be understood that steps of the process may be conducted in different chambers. For example the step of concentrating the nebulant (and/or a vapour) may be conducted in one chamber without pressure reduction and the step of contacting the article with the concentrated nebulant (and/or vapour) may be conducted in a different container.

The invention may be embodied in other forms and all such variations which will be apparent to those skilled in the art from the teaching hereof are deemed to be within the inventive concept herein disclosed.

The claims defining the invention are as follows:

1. A method for disinfecting or sterilizing an article or article part comprising:
    enclosing the article or article part inside a container having a wall of which at least a part is a semipermeable fabric or membrane;
    introducing an amount of vaporizable biocide as a nebulant to the interior of said container having the article or article part enclosed therein, the semipermeable fabric or membrane being selected to allow the biocide to pass from inside to outside of the container as a vapour at atmospheric pressure and to provide a barrier against entry of micro-organisms;
    concentrating the nebulized biocide such that the concentrated nebulized biocide comprises particles having biocide concentrations of at least 60 wt %;
    allowing biocide to exit the container through said semipermeable fabric or membrane while at or above atmospheric pressure; and
    exposing the article or article part to the concentrated nebulized biocide for a time sufficient to disinfect or sterilize the article or article part.

2. A method according to claim 1 wherein the vaporizable biocide introduced as a nebulant is prepared from a solution of hydrogen peroxide in a solvent.

3. A method according to claim 2 wherein a fluid is directed to flow generally parallel to the outside of the semipermeable fabric or membrane to expedite vapour removal from the interior side.

4. A method according to claim 3 wherein the fluid is air.

5. A method according to claim 4 wherein the fluid is humidity conditioned air.

6. A method according to claim 2 wherein the solvent is water.

7. A method according to claim 1 wherein the semipermeable fabric or membrane is selected from woven and non woven fabrics, sheets or films or combinations thereof in a single or multilayer structure and is hydrophobic or hydrophilic.

8. A method for disinfecting or sterilizing an article or article part comprising:
    enclosing the article or article part inside a container having a wall of which at least a part is a semipermeable fabric or membrane;
    introducing an amount of vaporizable biocide as a nebulant to the interior of said container having the article or article part enclosed therein, the semipermeable fabric or membrane being selected to allow the biocide to pass from inside to outside of the container as a vapour at atmospheric pressure and to provide a barrier against entry of micro-organisms;
    allowing biocide to exit the container through said semipermeable fabric or membrane while at or above atmospheric pressure;
    directing a fluid to flow generally parallel to the outside of the semipermeable fabric or membrane to expedite vapour removal from the interior side, wherein the fluid is humidity conditioned air; and
    exposing the article or article part to the nebulized biocide for a time sufficient to disinfect or sterilize the article or article part wherein the nebulized biocide comprises particles having biocide concentrations of at least 60 wt %.

9. A method according to claim 8 wherein the nebulant has a particle size distribution wherein more than 90% of the particles are in the range from 1-10 microns.

10. A method according to claim 8, further comprising concentrating the biocide after introducing the amount of vaporizable biocide as a nebulant to the interior of the container having the article or article part enclosed therein.

11. A method according to claim 8 wherein directing the fluid to flow generally parallel to-the outside of the semipermeable fabric or membrane expedites vapour pervaporation from the interior side.

12. A method according to claim 1 wherein the nebulant has a particle size distribution wherein more than 90% of the particles are in the range from 1-10 microns.

13. A method according to claim 1, further comprising concentrating the biocide after introducing the amount of vaporizable biocide as a nebulant to the interior of the container having the article or article part enclosed therein.

14. A method according to claim 3 wherein directing the fluid to flow generally parallel to the outside of the semipermeable fabric or membrane expedites vapour pervaporation from the interior side.

15. A method according to claim 2, further comprising concentrating the biocide by removing solvent from the inside of the container through the semipermeable fabric or membrane to the outside of the container.

16. A method according to claim 2 wherein the solution of hydrogen peroxide has a hydrogen peroxide concentration of at least 6 wt. %.

17. A method according to claim 16 wherein the hydrogen peroxide concentration is from 20-35 wt. %.

18. A method according to claim 17 wherein the hydrogen peroxide concentration is from 30-35 wt. %.

19. A method according to claim 8 wherein the vaporizable biocide introduced as a nebulant is prepared from a solution of hydrogen peroxide in a solvent.

20. A method according to claim 19 wherein the solution of hydrogen peroxide has a hydrogen peroxide concentration of at least 6 wt. %.

21. A method according to claim 20 wherein the hydrogen peroxide concentration is from 20-35 wt. %.

22. A method according to claim 21 wherein the hydrogen peroxide concentration is from 30-35 wt. %.

23. A method according to claim 1 wherein the semipermeable fabric or membrane comprises a copolymer of tetrafluoroethylene and perfluoro-3,6-dioxa-4-methyl-octene-sulfonic acid.

24. A method according to claim 8 wherein the semipermeable fabric or membrane comprises a copolymer of tetrafluoroethylene and perfluoro-3,6-dioxa-4-methyl-octene-sulfonic acid.

25. A method according to claim 1 wherein the article or article part is not exposed to temperatures above 60° C.

26. A method according to claim 8 wherein the article or article part is not exposed to temperatures above 60° C.

27. A method according to claim 1 wherein the method for disinfecting or sterilizing an article or article part does not comprise removing solvent vapour by vacuum pumping.

28. A method according to claim 8 wherein the method for disinfecting or sterilizing an article or article part does not comprise removing solvent vapour by vacuum pumping.

* * * * *